United States Patent
Theobald

(10) Patent No.: US 6,622,865 B1
(45) Date of Patent: Sep. 23, 2003

(54) DEVICE FOR PACKING PRESSURE-SENSITIVE ADHESIVE SUBSTRATE SECTIONS AND THE USE THEREOF

(75) Inventor: Frank Theobald, Bad Breisig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/889,132
(22) PCT Filed: Jan. 15, 2000
(86) PCT No.: PCT/EP00/00289
§ 371 (c)(1),
(2), (4) Date: Aug. 1, 2001
(87) PCT Pub. No.: WO00/43285
PCT Pub. Date: Jul. 27, 2000

(30) Foreign Application Priority Data

Jan. 21, 1999 (DE) .......................... 199 02 196

(51) Int. Cl.[7] ............................... B65D 57/00
(52) U.S. Cl. ...................... 206/447; 206/460
(58) Field of Search ................ 206/447, 440, 206/460, 713, 717, 720, 723, 813, 521

(56) References Cited

U.S. PATENT DOCUMENTS

| | | | |
|---|---|---|---|
| 3,498,448 A | * | 3/1970 | Kuster ........................ 206/440 |
| 4,887,611 A | | 12/1989 | Ruediger et al. |
| 5,115,913 A | * | 5/1992 | Anhauser et al. ............ 206/447 |
| 5,366,080 A | * | 11/1994 | Carstersen et al. ......... 206/723 |
| 5,423,737 A | * | 6/1995 | Cartmell et al. ............ 206/440 |
| 5,505,306 A | * | 4/1996 | Akemi et al. ................ 206/447 |
| 5,765,692 A | * | 6/1998 | Schenz ........................ 206/460 |
| 6,467,621 B1 | * | 10/2002 | Ishida ........................ 206/460 |

FOREIGN PATENT DOCUMENTS

| | | |
|---|---|---|
| DE | 1936607 | 2/1971 |
| DE | 39 21 434 | 1/1991 |
| EP | 0405393 B1 | 1/1991 |
| EP | 0 635 262 | 1/1995 |

* cited by examiner

*Primary Examiner*—Luan K. Bui
(74) *Attorney, Agent, or Firm*—Jordan and Hamburg LLP

(57) ABSTRACT

An apparatus provides for increasing storage stability of substrate portion which is provided with a self-adhesive layer covered by a carrier layer and which and are packed in bags. The adhesive layer is protected by the carrier layer which projects beyond the self-adhesive layer, at least in some areas The adhesive layer is protected from adhesive bonding with packaging material of the bag in that in projecting regions, on a side of the carrier layer assigned to the substrate portion, there are arranged elevations, fixed to the side-or shaped out from it, as spacers with respect to the bag, and, in addition to the elevations on that side of the carrier layer which is assigned to the substrate portion, elevations designed as spacers are arranged on an opposite side of the carrier layer.

12 Claims, 1 Drawing Sheet

DEVICE FOR PACKING PRESSURE-SENSITIVE ADHESIVE SUBSTRATE SECTIONS AND THE USE THEREOF

BACKGROUND

The invention relates to an apparatus for storage of substrate portions having a self adhesive layer covered by a carrier layer which are place in bags wherein protection from adhesive bonding with packaging material of the bags is provided by elevations on the carrier layer which function as spacers with respect to the bag.

The manufacture and use of sheet-like self-adhesive substrate portions formed of a substrate having an adhesive layer covered by a carrier layer is known. After they have been manufactured, there is the necessity to protect the substrate portions from loss of active material, for example as a result of evaporation, from the time at which they are stored until they are used. This is preferably achieved in that the self-adhesive substrate portions containing the active material, after their self-adhesive area has been covered, for the purpose of protection, wherein the carrier layer is a detachable carrier or protective layer, are sealed into a bag which encloses the substrates on all sides and is made of a material which is impermeable to the vapour phase. The carrier layer preferably projects beyond the self-adhesive area, which means that pulling off the carrier or protective layer is made easier.

One disadvantage of this package results from the fact that, during the storage of these substrate portions packed in this way, cold flow of the self-adhesive causes adhesive to emerge in the region around the substrate portion, and to cause the substrate to bond adhesively to the packaging material, as a result of which the removal of laminate of the packaging material, in the case of a bag packaged which is to be opened on only one side at a time of use, is made considerably more difficult or even impossible.

In these self-adhesive substrate portions, it is known to introduce an incision or a common tearing aid, for example in the form of a weakening, embrittlement or perforation, into the carrier layer, which makes the tearing open and detachment of the carrier layer easier or at all possible with a reasonable effort, and therefore aids the application of the self-adhesive substrate portions to the skin.

One disadvantage of this design of the package results from the fact that, during the storage of the substrate portions, cold flow in the region of the cut or weakening line causes self-adhesive components to emerge, which results in the substrate disadvantageously bonding adhesively to the surrounding packaging bag material. As a result, removing the laminate from the package opened on the one side is made considerably more difficult, or is even made impossible without damage.

EP 0 405 393 describes an apparatus for increasing the storage stability of sheet-like substrate portions which are equipped with a self adhesive and packed in bags and whose self-adhesive area is protected by a carrier layer projecting beyond it at least to some extent. Arranged in the carrier layer are space-maintaining elevations, specifically on the carrier layer, as spacers between the carrier layer and bag.

DE-A-19 36 607 discloses a rapid wound dressing which comprises a carrier strip provided with a self-adhesive layer, a wound pad applied thereto to cover the wound directly in the form of a cushion-like structure made of gauze, cellulose, fibrous fleece or similar material, and a protective material arranged above it. This last layer is designed as a sheet-like piece, which can be divided along a predetermined line. This dividing line is formed by a weakening of the material, such as a perforation or incisions.

SUMMARY OF THE INVENTION

Starting from the abovementioned prior art, the present invention is based on the object of specifying an apparatus for increasing a storage stability of substrate portions which are provided with a self-adhesive layer and are packed in bags. The apparatus prevents adhesive bonding of the substrate to the packing areas of the bag, even given comparatively long storage and in spite of cold flow of the self adhesive, and provides for the use of the unimpeded, easy removal of the substrate from the pack, which is opened on only one side.

In order to achieve the object, the present invention provides elevations on a side of the carrier layer on which is the substrate and elevations on an opposite side of the carrier layer wherein the elevations are designed as spacers to separate the carrier layer from the bag.

The spacers arranged on the side of and the opposite side of the carrier layer in accordance with the present invention provide an advantage, on the one hand, of a very uncomplicated type of package and, on the other hand, reliably prevent adhesive bonding between substrate and package, even during a comparatively long storage of sandwich-type laminates having an amorphous adhesive layer tending to cold flow between two solid layers. In particular in the presence of a detachment aid designed as a perforation line in the form of an incision or perforation in the carrier layer. The present invention eliminates the acute risk of adhesive bonding between the latter and the packaging material resting on it in an easy way and with simple means if, according to the present invention, there are space-maintaining elevations along the cut or weakening line.

BRIEF DESCRIPTION OF THE DRAWINGS

Further advantageous refinements of the present invention emerge from further features explained in more detail below using exemplary embodiments illustrated schematically in the figures, in which.

DETAILED DESCRIPTION

Figure 1:
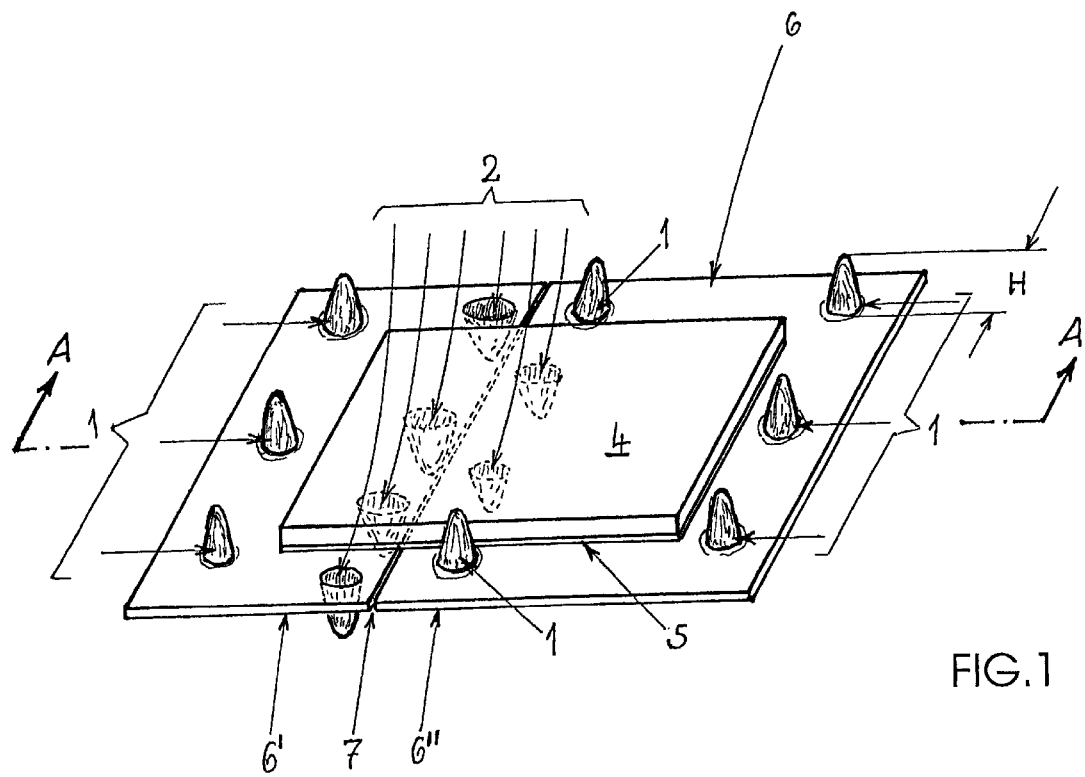
FIG. 1 shows a perspective illustration of a laminate, comprising a substrate with a self-adhesive coating and a carrier layer arranged on it, but without any packaging.
Figure 2:
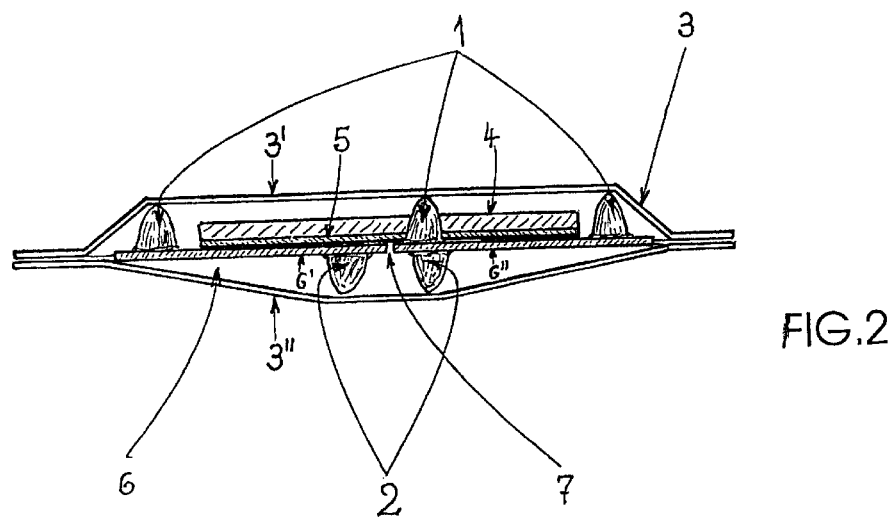
FIG. 2 shows a longitudinal section along a plane A—A, perpendicular to the area of the substrate, of a laminate with a substrate including adhesive layer and a carrier layer laminated to it, but with packaging.

An apparatus is illustrated in FIGS. 1 and 2 for increasing the storage stability of a substrate portion 4 provided with a self-adhesive layer 5 protected by a carrier layer 6 which is packed in a bag 3 according to FIG. 2. The carrier layer 6 has a projecting region which projects beyond the self-adhesive layer 5, at least in some areas. The self-adhesive layer 5 is protected from adhesive bonding with the packaging material in that in the projecting region, on that side assigned to the substrate portion 4, there are arranged elevations 1 fixed to the side or shaped out from it functioning as spacers with respect to the bag 3. If the carrier layer 6 has a weakening line 7, for example in the form of an incision or a perforation, as a detachment aid to make it easier to detach the carrier layer 6 from the self-adhesive layer 5, a risk of the carrier layer bonding adhesively to the material of the packaging bag 3 as a result of self adhesive emerging in cold flow must be countered by a design of the apparatus which is particularly suitable for this purpose. According to the present invention, this is achieved in that, in addition to the elevations 1 on that side of the carrier 6 which is assigned to the substrate portion 4, elevations 2 designed as spacers are arranged on an opposite side of the carrier layer 6.

An advantageous and expedient refinement provides for the carrier layer 6 to have at least two subareas 6' and 6" forming a common cut or weakening line 7 between them, and for there to be space-maintaining elevations 2 beside the cut or weakening line 7.

Accordingly, the designs shown by way of example in FIGS. 1 and 2 provide a laminate comprising a substrate portion 4 with a self-adhesive coating 5, which is covered by a carrier layer 6. Formed on the regions projecting beyond the substrate 4 are marginal elevations 1 whose height (H) projects beyond the substrate layer.

The carrier layer 6 has a weakening line or detachment aid in the form of a cut or a perforation 7, through which, during relatively long storage, self-adhesive material can emerge in cold flow and, as a result, could cause adhesive bonding between the carrier material or its underside and the material of the packaging bag 3.

In order to prevent this, and therefore to permit the easy removal of the laminate structure from the opened bag pack, according to the invention, elevations 2 are formed or arranged on that side of the carrier layer 6 opposite the elevations 1 on the underside in the present exemplary embodiment. These elevations 2 are used, as can best be seen from FIG. 2, to maintain a spacing between the carrier layer 6 and, in particular, the weakening line 7 present therein and lower packaging material layer 3", while the upper elevations 1 protect upper packaging material layer 3' in a manner known per se from adhesive bonding to self adhesive emerging at the edges of the self-adhesive layer 5.

In particular, the area regions 6' and 6" of the carrier layer 6 which are most at risk on its underside are protected from adhesive bonds by elevations 2 along the weakening line 7 and by elevations 2 arranged to be alongside these and offset from one another.

Further advantageous embodiments of the apparatus according to the invention are formed by the elevations being arranged alternately or in another pattern so as to point in both directions of the packaging material bag.

The exemplary embodiments of the invention shown in FIGS. 1 and 2 provide for the elevations 1 and 2 to consist preferably of hot-melt polymers, which can advantageously easily be deformed and do not exhibit any adhesiveness at room temperatures up to about 50° C. The use of the apparatus according to the invention, because of its high storage stability and its ability to be implemented in an uncomplicated manner, is particularly advantageously suited to the packaging of plasters, therapeutic systems and other substrates, especially sheetlike substrates, having a coating of self adhesive.

The invention is extremely expedient and achieves the object set at the beginning in an optimum way.

What is claimed is:

1. A packaged laminate, comprising:
   a substrate provided with a self-adhesive layer;
   a carrier layer covering the self-adhesive layer and having a projecting area projecting beyond the self-adhesive layer, the carrier layer having a first face on a side thereof at which the substrate is located and a second face on an opposite side thereof;
   the substrate, the self-adhesive layer, and the carrier layer forming a laminate structure;
   a bag enclosing said laminate structure;
   first elevations on the first face of the projecting area of the carrier layer and second elevations on the second face of the carrier layer, wherein the first and second elevations function as spacers spacing said laminate structure from said bag; and
   the carrier layer having a weakening line as an aid to detaching it from the self-adhesive layer.

2. The packaged laminate according to claim 1, wherein the carrier layer has at least two subareas divided by the weakening line and the second elevations are located along the weakening line.

3. The packaged laminate according to any of claim 1 or 2, wherein the carrier layer include at least one hot-melt polymer which does not exhibit any adhesiveness at room temperature up to about 50° C. and the first and second elevations are formed from said carrier layer.

4. The packaged laminate according to any of claim 1 or 2, wherein the first and second projections include individual moldings of material which is non-adhesive at room temperature up to about 50° C., the first and second projections being affixed to the carrier layer by means of a permanent adhesive or heat-sealing material.

5. The packaged laminate according to claim 2, wherein the weakening line extends transversely through the carrier layer and the second elevations are formed along the weakening line are in the subareas of the carrier layer.

6. The packaged laminate according to claim 5, wherein the second elevations are arranged offset from one another along the weakening line.

7. The packaged laminate according to any of claim 1 or 2, wherein the second elevations are arranged alternately on sides of the weakening line.

8. The packaged laminate according to any of claim 1 or 2 in which the substrate is a sheet having a coating.

9. The packaged laminate according to claim 1, wherein the weakening line is in the form of incisions or perforations.

10. The packaged laminate according to claim 8, wherein the coating is a self-adhesive.

11. The packaged laminate according to claim 10, wherein the substrate is a plaster or a therapeutic system.

12. The packaged laminate according to claim 1, wherein the weakening line is a cut in the carrier layer.

* * * * *